United States Patent
Troy et al.

(10) Patent No.: US 9,182,487 B2
(45) Date of Patent: Nov. 10, 2015

(54) ADVANCED REMOTE NONDESTRUCTIVE INSPECTION SYSTEM AND PROCESS

(75) Inventors: James J. Troy, Issaquah, WA (US);
Scott W. Lea, Renton, WA (US); Gary E. Georgeson, Tacoma, WA (US);
William P. Motzer, Seattle, WA (US);
Peter J. Hellenbrand, Seattle, WA (US);
Kevin Puterbaugh, Auburn, WA (US)

(73) Assignee: The Boeing Company, Chicago, IL (US)

( * ) Notice: Subject to any disclaimer, the term of this patent is extended or adjusted under 35 U.S.C. 154(b) by 671 days.

(21) Appl. No.: 13/166,613

(22) Filed: Jun. 22, 2011

(65) Prior Publication Data

US 2012/0327187 A1   Dec. 27, 2012

(51) Int. Cl.
| | |
|---|---|
| *G01S 15/89* | (2006.01) |
| *G01N 29/06* | (2006.01) |
| *G01S 17/88* | (2006.01) |
| *G01N 29/04* | (2006.01) |
| *G01N 29/26* | (2006.01) |
| *G01N 29/30* | (2006.01) |
| *G01N 29/44* | (2006.01) |

(52) U.S. Cl.
CPC .......... *G01S 15/8938* (2013.01); *G01N 29/043* (2013.01); *G01N 29/0654* (2013.01); *G01N 29/262* (2013.01); *G01N 29/30* (2013.01); *G01N 29/4472* (2013.01); *G01S 17/88* (2013.01)

(58) Field of Classification Search
None
See application file for complete search history.

(56) References Cited

U.S. PATENT DOCUMENTS

| | | | |
|---|---|---|---|
| 4,774,842 A | 10/1988 | Kollar et al. | |
| 7,859,655 B2 | 12/2010 | Troy et al. | |
| 2005/0264881 A1* | 12/2005 | Takagi et al. | 359/463 |
| 2008/0109187 A1 | 5/2008 | Kollgaard et al. | |
| 2009/0010489 A1* | 1/2009 | Appel et al. | 382/100 |
| 2009/0086014 A1 | 4/2009 | Lea et al. | |
| 2010/0228506 A1* | 9/2010 | Motzer et al. | 702/56 |
| 2011/0137615 A1 | 6/2011 | Motzer et al. | |
| 2013/0063563 A1* | 3/2013 | Pulla et al. | 348/46 |

* cited by examiner

*Primary Examiner* — Frederick Bailey
(74) *Attorney, Agent, or Firm* — Felix L. Fischer

(57) ABSTRACT

A system for inspecting a test article incorporates a diagnostic imaging system for a test article. A command controller receives two dimensional (2D) images from the diagnostic imaging system. A three dimensional (3D) computer aided design (CAD) model visualization system and an alignment system for determining local 3D coordinates are connected to the command controller. Computer software modules incorporated in the command controller are employed, in aligning, the 2D images and 3D CAD model responsive to the local 3D coordinates. The 2D images and 3D CAD model are displayed with reciprocal registration. The alignment system is then directed to selected coordinates in the 2D images or 3D CAD model.

18 Claims, 5 Drawing Sheets

ADVANCED REMOTE NONDESTRUCTIVE INSPECTION SYSTEM AND PROCESS

REFERENCE TO RELATED APPLICATIONS

This application is copending with application Ser. No. 11/555,953 entitled REMOTE NONDESTRUCTIVE INSPECTION SYSTEMS AND METHODS filed on Nov. 2, 2006 by Jeffrey R. Kollgaard, Gary E. Georgeson, Blake A. Bertrand, and Richard H. Bossi, application Ser. No. 11/863,755 entitled LOCAL POSITIONING SYSTEM AND METHOD filed on Sep. 28, 2007 by Scott W. Lea, Gary E. Georgeson, James J. Troy, M. Matsen, J. Hansen and C. Richards, application Ser. No. 12/897,408 entitled METHODS AND SYSTEMS FOR LOCATING VISIBLE DIFFERENCES ON AN OBJECT filed on Oct. 4, 2010 by James J. Troy and Scott W. Lea, application Ser. No. 13/036,619 entitled DISTRIBUTED OPERATION OF A LOCAL POSITIONING SYSTEM filed on Feb. 28, 2011 by James J. Troy and Scott W. Lea, which have a common assignee with the present application and which are incorporated herein by reference as though fully set forth.

BACKGROUND INFORMATION

1. Field

Embodiments of the disclosure relate generally to the field of non-destructive testing and more particularly to embodiments for an apparatus and method for measurement and viewing with a local positioning system (LPS) and two dimensional (2D) images of non-destructive inspection (NDI) scans of a test article remotely with three dimensional (3D) Computer Aided Design (CAD) model presentations in combination with 2D images of NDI scan results for enhanced visualization.

2. Background

Non-destructive testing and results analysis of manufactured articles such as aircraft requires participation by specially trained NDI experts. Prior processes required NDI experts to be on-site with the test article (airplane) and NDI scanning hardware to obtain the necessary testing results. In addition, since the scanning hardware was not aligned with the local coordinate system of the test article, manual/subjective alignment was used to determine the local position and orientation of the scan relative to the target. Also, field measurements of positions of interest on the test article were usually made with processes such as using location inference and distances were measured from nearby landmarks using tape measures. These methods do not provide desired measurement precision for accurate analysis of test results. Additionally, the NDI data obtained required manual association with actual relative position of the structure of the test article for interpretation and analysis.

It is therefore desirable to provide a system allowing accurate placement of NDI scanning equipment and integrated visualization of NDI results with 3D CAD models of structure of the test article for enhanced analytical capability and accuracy with reduced cost.

SUMMARY

Embodiments described herein provide a system for inspecting a test article incorporating a diagnostic imaging system for the test article. A command controller receives two dimensional (2D) images from the diagnostic imaging system. A three dimensional (3D) computer aided design (CAD) model visualization system and a 3D measurement and alignment system for determining positions defined in the local 3D coordinate system of the test article are connected to the command controller. Computer software modules incorporated in the command controller are used to align the 2D images and 3D CAD model responsive to the local 3D coordinates creating positional correspondence between the 2D scan images and the 3D environment. The 2D images and 3D CAD model are displayed with reciprocal registration. The position measurement system can be directed to selected coordinates in the 2D images or 3D CAD model. Alternately, 3D positions measured by the 3D measurement system can be displayed on the 2D image or in the 3D CAD model environment.

In one example embodiment, a remote non-destructive inspection (NDI) system includes a NDI scanner mountable to a test article at a local site and a 3D measurement instrument, such as a local positioning system (LPS) positioned adjacent the test article. A 3D CAD visualization application for display of 3D CAD models of the test article is provided and a remote command controller is connected to the NDI scanner, the LPS and the 3D CAD visualization tool. The remote command controller has software modules for receiving 2D scan images from the NDI scanner, receiving 3D coordinate data from the LPS, aligning the NDI scan images and 3D CAD model responsive to the local 3D coordinates, displaying the images and 3D CAD model with reciprocal registration, and positioning the LPS.

The embodiments allow a method for remote non-destructive inspection (NDI) wherein a NDI scanner mountable to a test article is placed at a local site. A local positioning system (LPS) is positioned adjacent the test article and the NDI scanner, LPS and a three dimensional (3D) computer aided design (CAD) visualization application for display of 3D CAD models of the test article are connected to a remote command controller. A desired position for the NDI scanner on the test article is indicated with the LPS from the command controller. Scan data from the NDI scanner is then received and 2D scan images are created. The LPS is calibrated for transmission of 3D coordinates of the test article to the remote command controller. The remote command controller then calculates a scan registration matrix for 2D data from the NDI scanner to 3D coordinates and an inverse scan registration matrix for 3D coordinates in the CAD model to display in the 2D scan images. The 3D CAD model and 2D scan images are then displayed with reciprocal registration of selected points. The LPS may then be re-directed responsive to a selected point in the 2D scan image or 3D CAD model with a set of 3D coordinates from the command controller.

The features, functions, and advantages that have been discussed can be achieved independently in various embodiments of the present invention or may be combined in yet other embodiments further details of which can be seen with reference to the following description and drawings.

DETAILED DESCRIPTION

The embodiments described herein provide a remote acquisition and analysis system for non-destructive inspection (NDI) employing multiple hardware and software components networked through a central analysis interface. The integration of these components enables a remote operator to acquire and analyze NDI data using automated scanning equipment and a local positioning system (LPS), and then visualize and interact with the data in 2D and 3D analysis software. Alignment points measured by the LPS in the scanning area are used to create a positional correspondence for setup of the scanning equipment and registering the resulting 2D scan data in the coordinate system of a 3D CAD model visualization environment.

The ability to operate all of the hardware and software components remotely enables data collection by an expert NDI analyst from an off-site operations center, with the only on-site assistance coming from non-expert support personnel to setup the LPS and NDI scanning hardware.

Figure 1:
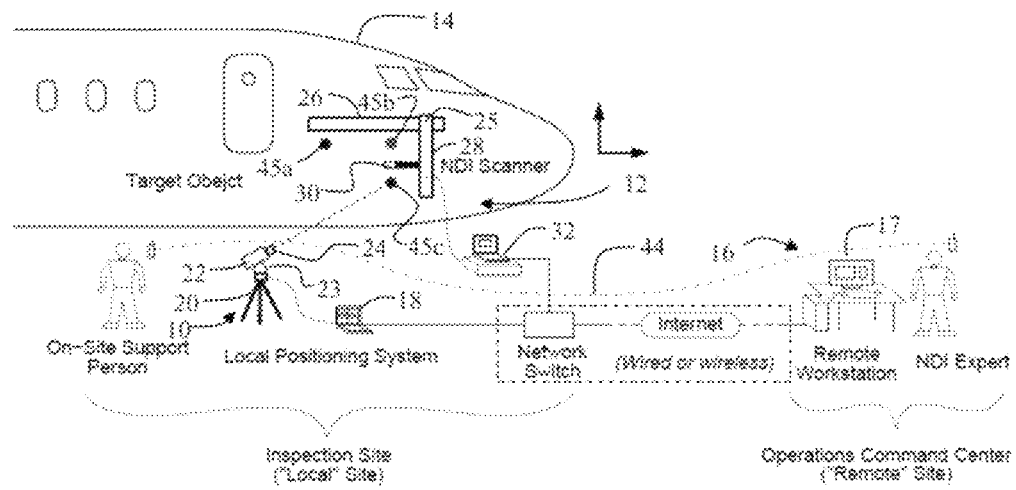
FIG. 1 is pictorial representation of an embodiment of the remote non-destructive inspection system including the local site and remote site components.
Figure 2:
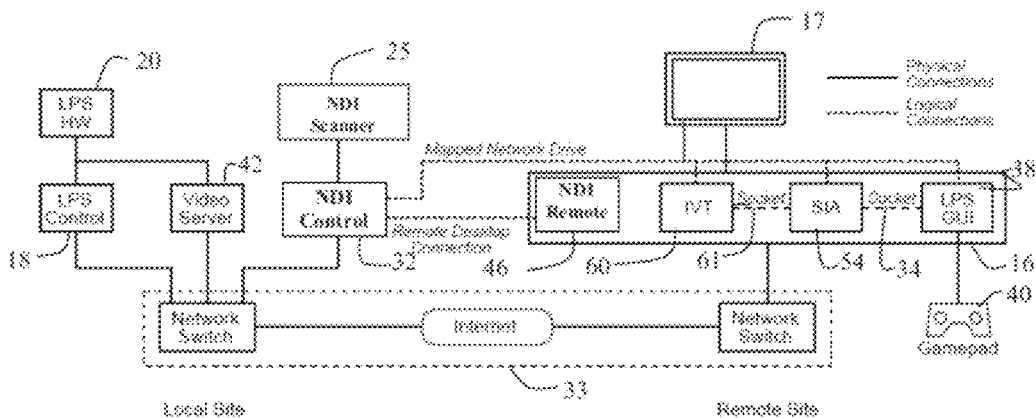
FIG. 2 is a block diagram of the physical and logical connections between the system components.

The primary on-site and off-site hardware components are shown in FIG. 1 with a schematic of system interconnection shown in FIG. 2. An alignment system for determining local 3D coordinates of a test article such as an LPS 10 and a diagnostic imaging system such as a NDI scanner 12 are located at the inspection site (referred to herein as the "local site") for the article being inspected, aircraft 14. A remote command workstation 16 to be operated by the NDI expert is located at an operations command center (referred to herein as the "remote site") with a master display 17. For the example embodiment described herein the LPS incorporates a controller 18, typically a personal computer (PC), and a servo controlled video, distance measurement, and pointing system 20 having a video camera 22 mounted to a pan-tilt unit 23 and incorporating a laser pointer 24 which may also have functionality as a laser range meter for highly accurate distance measurement.

An LPS structure and operational description applicable for use in the embodiment described herein is provided in application Ser. No. 11/863,755 entitled LOCAL POSITIONING SYSTEM AND METHOD, U.S. Pat. No. 7,859,655 entitled METHOD INVOLVING A POINTING INSTRUMENT AND TARGET OBJECT and application Ser. No. 13/036,619 entitled DISTRIBUTED OPERATION OF A LOCAL POSITIONING SYSTEM, the disclosures of which are incorporated herein by reference.

An example NDI scanner 12 for use in the embodiment described herein is a Mobile Automated Ultrasonic Scanner (MAUS®) by the Boeing Company and available through NDI Solutions, Inc. (NDTS), New Richmond, Wis. which incorporates a scanning unit 25 having a support rail 26 mountable to the test article and a translation rail 28 supporting an ultrasonic head 30. The translation rail moves along the support rail for a first axis of scan ad the head moves along the translation rail for a second orthogonal axis of scan. The NDI scanning unit is controlled by a second control PC 32. In alternative embodiments a hand held scanner may be employed such as a phased array ultrasonic transducer (UT) system with positional encoders.

For conducting remote NDI operations, tasks at the inspection site include removing the LPS 10 and NDI scanner 12 from shipping/storage containers, setting up the LPS, attaching the NDI scanning unit 25 to the airplane 14, and connecting the control PCs 18, 32 to the interact 33 shown in FIG. 2. Internet connection of the control PCs may be wired or wireless. After setup, the LPS allows an NDI expert at the remote site to help guide the rest of the process as will be described in greater detail subsequently. Once the control PC 18 is started, an automated process will send the on-site network domain information back to the operations center at the remote site.

When the on-site setup of the LPS is compete, the NDI expert at the remote operations site connects to the LPS control PC 18 through a network socket connection 34 in the remote workstation 16 to operate the LPS pan-tilt unit 23, camera 22, and laser range meter/laser pointer 24 using a LPS graphical user interface (GUI) 38 and manual controller 40. A video connection is also established through an LPS video server 42. The visual display of the LPS GUI and associated video from the LPS are displayed on the master display 17. If the IP address of the video server is unknown, a separate network discovery process is launched to determine the IP address based on the device MAC address. The LPS GUI 38 allows communication from the LPS 10 of position data as well as camera/video data to the remote command workstation 16 and control of the LPS for positioning and operation of the camera 22 and laser pointer 24 from the remote command workstation. Once the remote connection is established, the LPS 10 can be used as an integral system element to communicate with the our-site support technician to help guide the setup of the NDI scanner 14. The NDI expert can direct the on-site support technician to place the NM scanning unit 25 in the proper position on the aircraft 14 using the LPS laser pointer 24 while viewing with camera 22 (along with an audio channel 44 provided by a microphone built into the camera unit, cell phones or similar devices or a land line telephone). This type of remote interaction is sometimes referred to as telepresence.

Once the NDI scanning unit 25 is in the proper position and the NDI control PC 32 is setup and connected to the internet, the on-site support technician is directed to place three alignment marks 45a, 45b and 45c using a marker, such as an adhesive-backed sticker, within the scan region. The NDI expert will point out these locations with the LPS laser pointer 24 remotely controlled through the LPS GUI 38 and manual controller 40. These alignment marks are visible to the NDI expert through the LPS video camera 22 and will also show up in the NDI scan as will be described in greater detail subsequently. Alternatively, alignment points on the NDI scanning device itself can be used instead of alignment marks attached to the test article.

The NDI scanner 12 is connected from the internet through a remote desktop display application 46, such as Windows Remote Desktop Connection, which interfaces to the NDI control PC 32 for the NDI scanning unit 25. Other types of connections, such as a socket connection, would also be possible, if supported by the NDI control application. The software module for the Scan Integration Application (SIA) 54 allows communication of NDI scan data to the remote command workstation 16 and control of the NDI scanner 12 from the remote command workstation. The NDI expert sets the scanning software parameters, and begins the scan. In an example operational scenario, as the NDI scanning device is operating, the remote NDI expert calibrates the LPS to the airplane coordinate system (using the LPS calibration process described in U.S. Pat. No. 7,859,655) to obtain a calibration matrix, and then measures the three scan alignment marks 45a, 45b and 45c as location reference calibration points shown in FIG. 1 with the LPS 10. Images and video from the LPS camera can also be recorded. When the NDI scan is complete the remote NDI expert saves and transfers the 2D scans to the remote command workstation 16.

Figure 3:
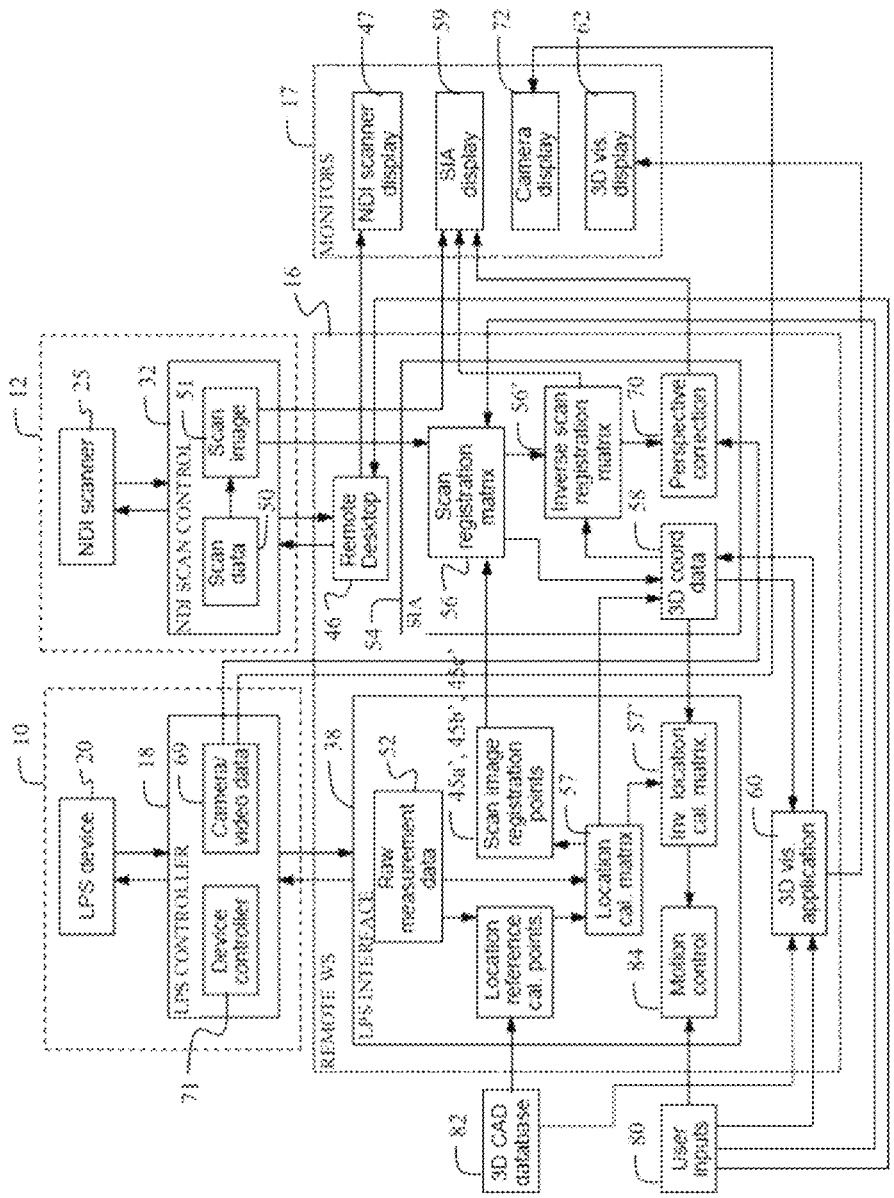
FIG. 3 is a block diagram of the interactive connection of software modules and hardware elements in the system.

As shown in FIG. 3, the 2D NDI scan data 50 presented as a scan image 51 and the LPS measured data 52 including measurements of the alignment marks are received from the NDI system 12 and LPS system 10. A scan integration and display application software module on the remote command workstation 16, which is referred to herein as the Scan Integration Application (SIA) 54 provides software modules for integration of the data. This software computes a scan registration matrix 56 based on the 2D scan image registration points 45a', 45b' and 45c' and the 3D location reference calibration points 45a, 45b and 45c based on the calibration matrix 57 to provide a direct mapping between 2D pixel coordinates of the NDI scan data and the 3D coordinate system data 58 of the test article (the aircraft 14 in the described example). This allows the 3D location reference calibration points to define a planar surface on the test article that corresponds to the surface of the scanned data. The scan registration matrix 56 is computed using a common point alignment process between the 2D pixel coordinates and the 3D alignment points.

Creation of the scan registration matrix is accomplished by reformulating as an offset problem involving two 3D coordinate systems that are related by three common points (the location reference calibration points 45a, 45b and 45c). A depth value is assigned to the scan images of the points (scan image registration points 45a', 45b' and 45c') in order to create a virtual third dimension for the 2D image. The same vector-based approach described in U.S. Pat. No. 7,859,655 may then be employed to solve for the relative offset transformation matrix.

The general process for mapping between the 2D image space and 3D coordinates of the target object can be performed using the following process. Given a pixel-based image with a known aspect ratio and 3D coordinates associated with 3 non-collinear positions that are identifiable in the image, the 4×4 homogeneous transformation matrix that maps between the 2D image coordinates and the 3D coordinate system is created using the following scenario to reformulate the problem into an offset problem involving two 3D coordinate systems that are related by three common points.

Initially, the pixel values of the three points of interest in the 2D image are determined. This can be done with manual selection (the NDI expert picking the points on the screen) or with image processing software that can locate reference shapes in the image. A depth value is then assigned to each of the scan image points in order to create a virtual 3D dimension to the 2D image. Since three points have been created as the location reference calibration points 45a, 45b and 45c, and three points define a plane, an assumption is made that the image is planar. (If the scan region in the image is not planar, additional points would need to be taken). A convenient selection for the depth values is to set them all to zero. Two sets of 3D points are then used to solve for the relative 4×4 homogeneous transformation matrix which is defined as the scan registration matrix 56. A 3-point vector based technique is employed as described in U.S. Pat. No. 7,859,655 and also described below:

The basic form of a 4×4 homogeneous transformation matrix is shown in Equation 1.

$$_A^B T = \begin{bmatrix} r_{11} & r_{12} & r_{13} & X \\ r_{21} & r_{22} & r_{23} & Y \\ r_{31} & r_{32} & r_{33} & Z \\ 0 & 0 & 0 & 1 \end{bmatrix} \quad \text{Eqn 1}$$

In the above equation, $_A^B T$ represents the transformation of coordinate system A relative to coordinate system B. This matrix can then be used to pre-multiply a position vector defined, in one coordinate system, into a vector defined in the other, as shown in Equation 2.

$$^B P = {_A^B T} {^A P} \quad \text{Eqn 2.}$$

Where $^B P$ is the vector defined in coordinate system B after the transformation matrix $_A^B T$ has been applied to the point defined in coordinate system A. $^A P$. The inverse $_A^B T = (_A^B T)^{-1}$ can be used to transform B into A, as shown in Eqn 3.

$$^A P = (_A^B T)^{-1} {^B P} = {_B^A T} {^B P} \quad \text{Eqn 3.}$$

There are multiple ways to compute transform $_A^B T$. For situations where the direction and length of the vectors to the calibration points are known the minimum number of points required is three, assuming that they are not co-linear. The basic 3-point technique is described below:

$n_A = V_{A12} \times V_{A13}$ $n_B = V_{B12} \times V_{B13}$ $\text{axis}_1 = n_A \times n_B$ $\text{ang}_1 = a\cos(|nA| - |nB|)$ $\text{Rot}_1 = f_1(\text{ang}_1, \text{axis}_1)$ $\text{axis}_2 = V_{A12} \times V_{B12}$ $\text{ang}_2 = a\cos(|V_{A12}| - |V_{B12}|)$ $\text{Rot}_2 = f_1(\text{ang}_2, \text{axis}_2)$ $\text{Rot}_{12} = \text{Rot}_1 \text{Rot}_2$ $_A^B T = [\text{Rot}_{12} \text{Rot}_1 V_{B12} - V_{A12}]$ $_B^A T = (_A^B T)^{-1}$ Where $f_1()$ is the function which generates a 3×3 rotation matrix from the angle-axis definition (this is a well known mathematical formulation). Note that $_B^A T$ only needs to be computed once for any position of the LPS relative to the target object, and can then used to convert any number of vectors from coordinate system A (the scan image) into coordinate system B (the 3D coordinate system).

Figure 4:
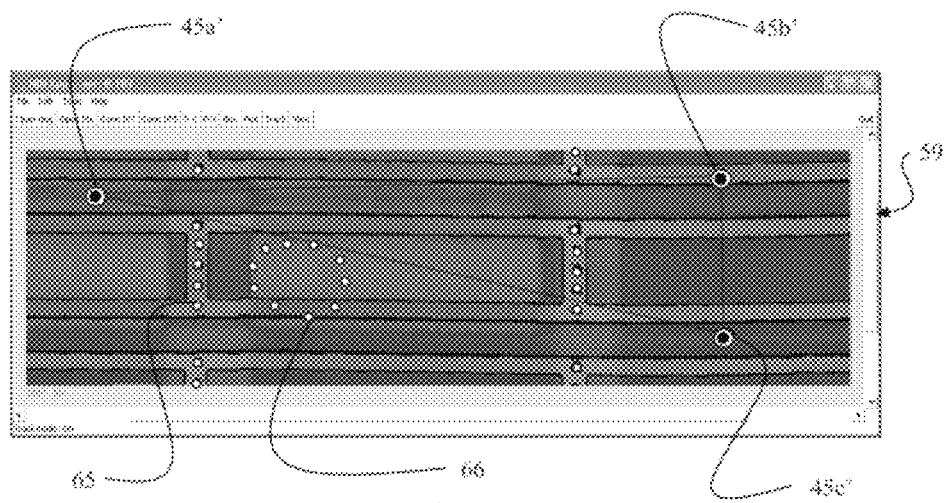
FIG. 4 is a view of the Scan Integration Application scan data display.

The inverse of the scan registration matrix 56' is used for the reverse process, which projects 3D coordinates from the 3D environment onto the 2D scan image. A 2D scan image can be presented by the SIA in an SIA display field 59 on master display 17 as shown in FIG. 4. With the 2D/3D registration computed by the scan registration matrix, any point selected on the 2D scan display can be converted into the corresponding 3D coordinates of the test article (e.g. airplane coordinates, or 3D point converted into 2D pixel coordinates, defined herein as reciprocal registration of the images. As an example, representations of the scan image registration points 45a', 45b' and 45c' of the three alignment marks 45a, 45b and 45c on the aircraft (shown in FIG. 1) are shown. A connection to a 3D CAD model visualization application 60 such as the Boeing developed Integration Visualization Tool (IVT) is provided through a network socket connection 61 (the logical connection represented in FIG. 2). For the example embodiment, the socket connection to IVT is through a plug-in interface that can send and receive object position and orientation data, virtual camera position and orientation data, and selection point positions.

Figure 5:
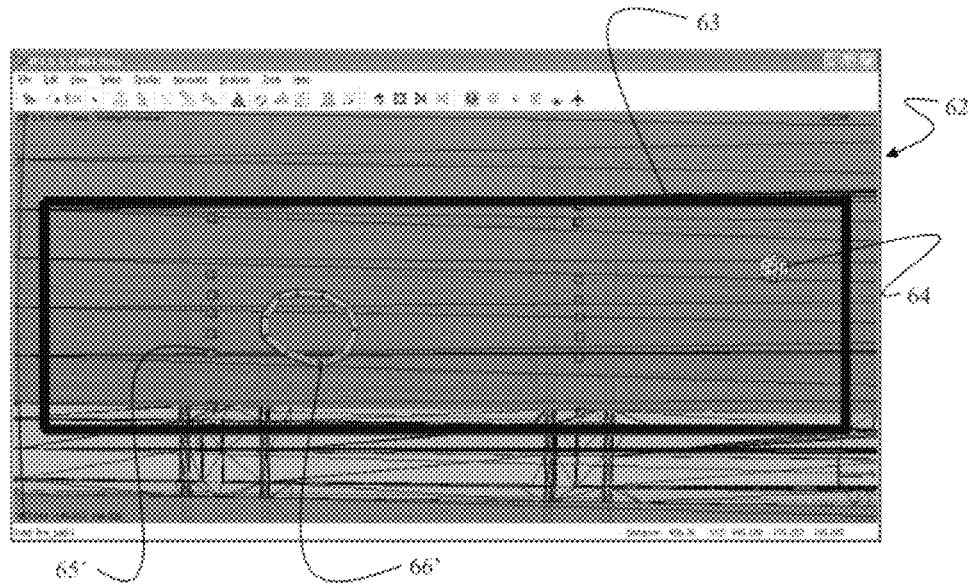
FIG. 5 is a view of the Integrated Visualization Tool 3 dimensional display.

After the connection is established with the 3D visualization application, the SIA provides 3D coordinates to the 3D visualization application to align the virtual camera with the proper target coordinates, so that a presented 3D view in a 3D visualization display field 62 on the master display 17 is perpendicular to the surface at the scan location as shown in FIG. 5. A rectangular frame object 63, used as a reference to outline the region or sub-region of the NDI scan area, is loaded into the 3D visualization application for visualization on the master display 17. The NDI expert can make user inputs (represented as 80 in FIG. 3) to manipulate both the 2D and 3D presentations. The expert can point to specific locations in the 3D environment using a real-time proxy cursor 64 controlled from the SIA. Point objects 65 and poly-line geometry such as line 66 shown in FIG. 4 can be drawn in the SIA display and imported into 3D visualization display showing as points 65' and line 66' in FIG. 5. Similarly, point selection from the 3D visualization application 60 can also be displayed in the SIA display 59 as 3D coordinate data 58 passed through the inverse scan registration matrix 56' to create a properly registered 2D point on the scan image. The view in 3D visualization can be pivoted around the proxy cursor 64 if necessary to see other views of the 3D models. Other information, such as part numbers, dimensions, etc., can also be acquired from the 3D model database 82 and displayed by 3D visualization application 60 on 3D visual display 62.

Simultaneously the real-time socket connection 34 to the LPS can be employed by the remote NDI expert through motion control 84 to move the LPS pan-tilt unit 23 (shown in FIG. 1) to point the laser pointer 24 at a specific 3D location selected on the SIA display 59 or 3D visual display 62 and provided by the SIA from the 3D Coordinate Data 58 through an inverse calibration matrix 57' by motion control 84 in the LPS interface 38 to the LPS controller 18 in the LPS 10 Measurements using the range meter function of the laser pointer 24 and camera/video data 69 from camera 22 in the LPS device can also be requested through the LPS interface directly as a user input 80. With this connection enabled, it is possible to select a point on an object in the 3D environment of 3D visual display 62 and have the position show up in the SIA display 59 and also move LPS 10 to point at the location on the actual object with the laser pointer 24 using device controller 71.

In addition to NIX scans, the Silk can also display perspective-corrected images of camera/video data 69 in the SIA display 59 on the master display 17 to show visible surface information in the scanned region aligned in airplane coordinates. The SIA computes perspective correction 70 by using the camera image, the zoom value and optical properties of the camera, the relative position and orientation transformation from the initial LPS calibration process, the current direction vector of the LPS camera, and surface point measurements in the region of the image such as the points used to register the NDI scan). This provides the positional correspondence between the 2D image and the 3D coordinate system of the target object, which allows the NDI expert to select visible image locations presented on the SIA display 59 on the master display 17 to determine corresponding 3D data.

Figure 6:
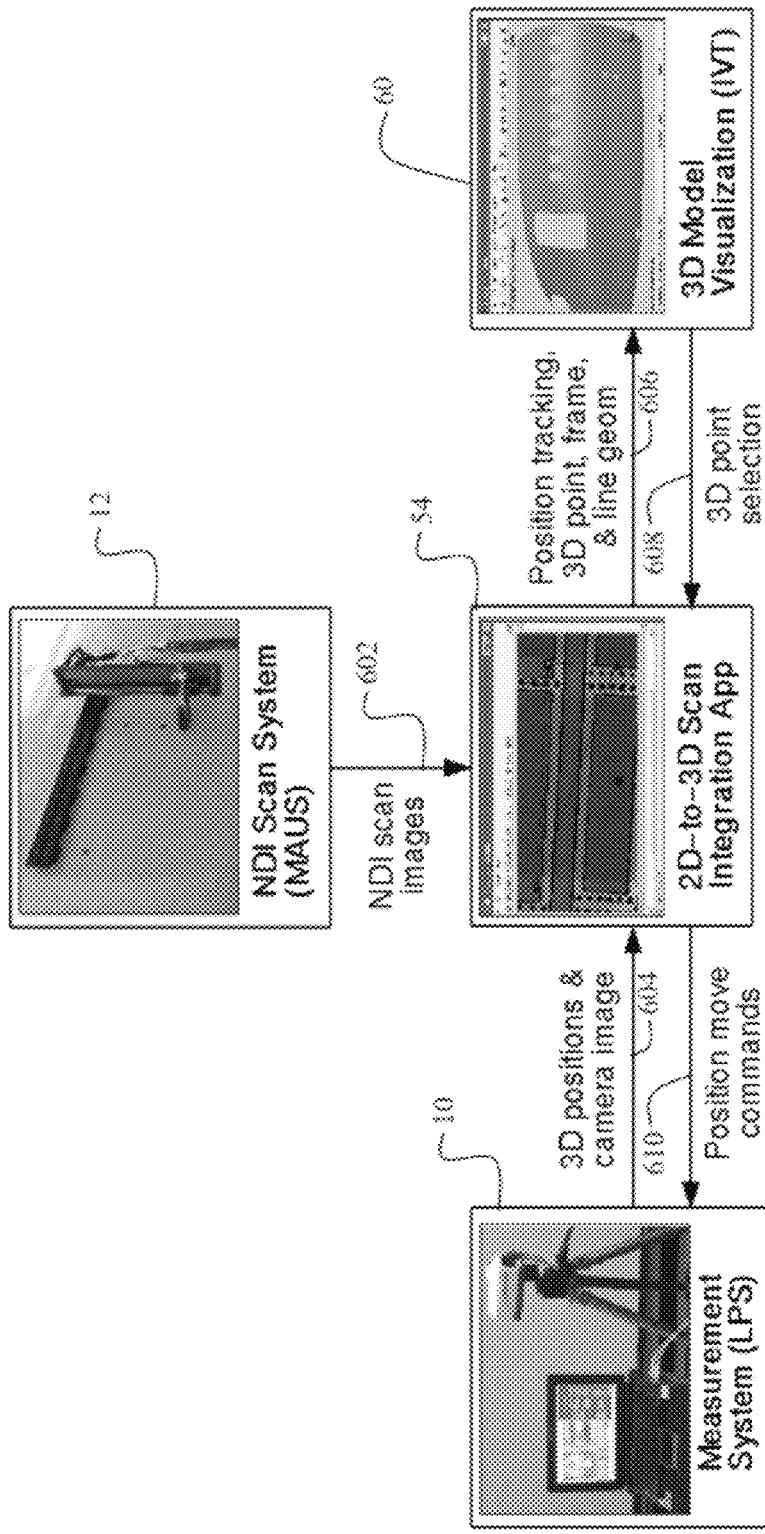
FIG. 6 is a process flow representation for data and control.

The data interchange described is shown in the process flow chart of FIG. 6. NDI scan image data is received from the NDI Scan System 12 by the SIA 54 as represented by arrow 602. 3D positions from the actual aircraft test article and camera images are provided flora the LPS 10 to the SIA 54 as represented by arrow 604. As previously described, the SIA creates 2D to 3D conversion of the scan data based on the scan registration matrix and presents the scan data and 3D visualizations on the display 17. The position tracking, 3D point, scan frame and line geometries are then provided by the SIA to the 3D visualization application 60 for registration of the positioning in the 3D model, as represented by arrow 606, with 3D visualizations then presented by the 3D visualization application on the master display 17. 3D point selection within the 3D visualization application is provided back to the SIA as represented by arrow 608. The SIA, using the inverse scan registration matrix, can then present the selected point information on the master display 17 for registration in the scan data view. Additionally, the 3D point selection is provided by the SIA to the LPS as position move commands, represented by arrow 610, to orient the LPS laser pointer on the aircraft at the point represented by the 3D point selection. Camera/video data of the selected point can then be transmitted back to the SIA for display on the master display 17 allowing the remote NDI expert to view the physical test article at the locations corresponding to the selected point. This allows data overlap of all three elements, NDI scan, 3D CAD visualization and actual real view of the aircraft test article for analysis by the NM expert at the remote site. The scan registration matrix convert converts 2D scan image coordinates into 3D coordinate data, and the LPS device location calibration matrix also converts LPS device coordinates into 3D coordinate data: The 3D coordinate system available through the CAD database provides the common link between the two. The data flows for reciprocal registration provided by the embodiments described are: 2D scan image coordinates through the scan registration matrix to 3D coordinate data through the LPS inverse location calibration matrix to LPS device coordinates, and LPS coordinates through the LPS location calibration matrix to 3D coordinate data through the inverse scan registration matrix to 2D coordinates for the SIA display.

Figure 7:
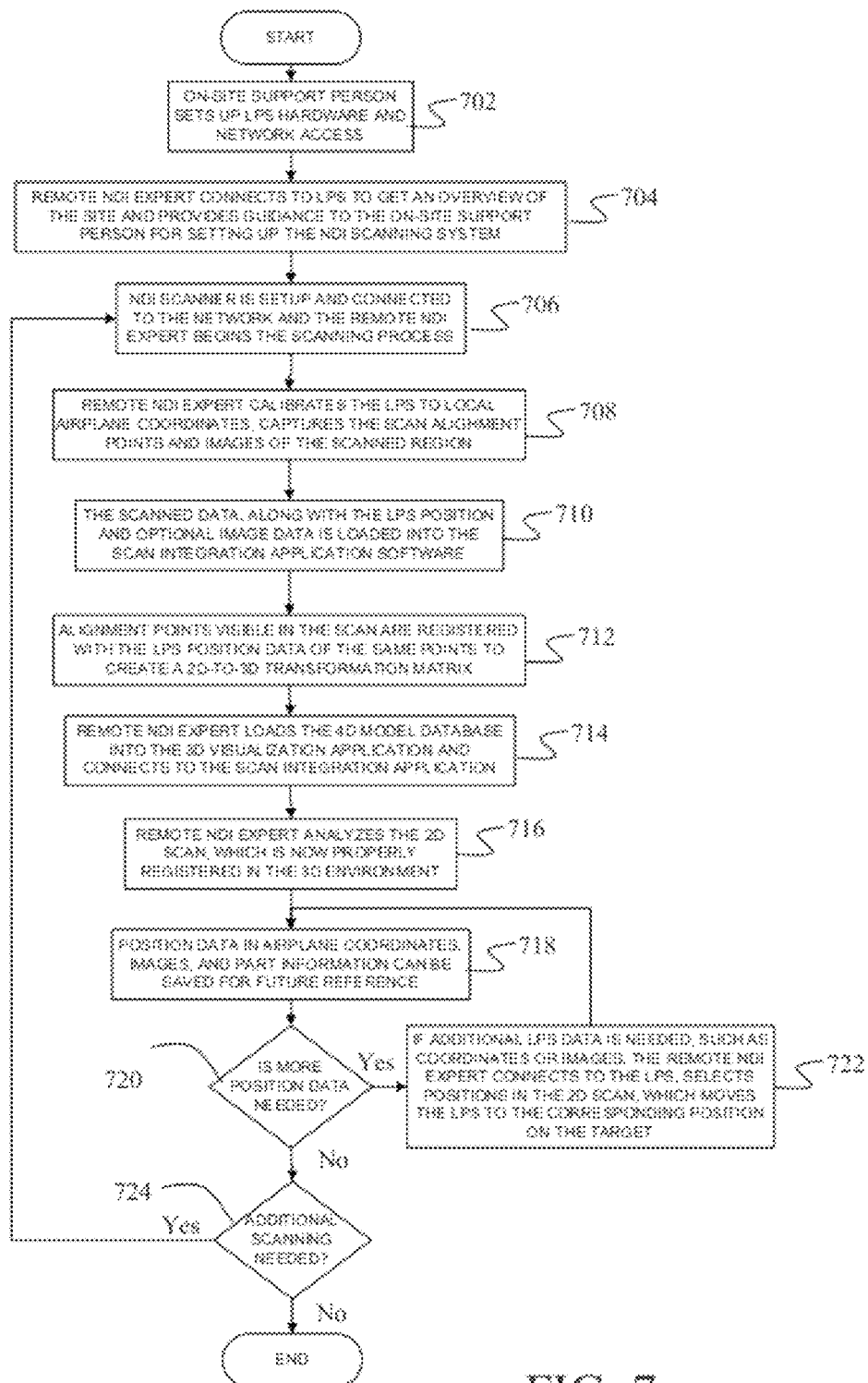
FIG. 7 is a flowchart of method steps for employing the described embodiment.

The basic method allowed by the embodiment of the system described herein is shown in FIG. 7. Setup the LPS (including taking it out of box), have support person point it at the airplane, and connect to internet, step 702. The remote NDI expert can then view the test article (airplane) and tell on-site support person reposition LPS, if necessary, and directs on-site support person to place the NDI scanning system (such as the MAUS) in correct position, as well as the locations to place the three scan alignment marks, using remote control of laser pointer, step 704. The on-site support person assembles the rest of the NDI scanning system hardware and attaches safety cable, then connects the NDI scanning control PC to internet, the remote NDI expert connects to NDI scanning control PC using remote desktop and sets scan parameters and starts NDI scanning process, step 706. The remote NDI expert calibrates the LPS (as described in U.S. Pat. No. 7,859,655) to airplane coordinates using the LPS and then acquires positions of the three scan alignment points, step 708. The scan completes and the remote NDI expert saves scan data files with LPS position data and optional image data and loads the 2D NDI data and 3D alignment points into the scan integration application (SIA), step 710. At the remote command center the NDI expert uses the SIA to perform a 2D-to-3D registration process using the visible alignment points to create a scan registration matrix, step 712. This matrix is generated using a 3-point alignment process (as described in U.S. Pat. No. 7,859,655). With registration complete, the remote NDI expert starts the 3D visualization application (such as IVT), establishes connection to the 3D visualization application, loads the 3D model database, and sends the viewpoint command to align IVT view with 2D scan image, step 714. The remote NDI expert then analyzes the 2D scan which is now properly registered in the 3D environment, which allows the remote NDI expert to move the 2D cursor in the SIA display which simultaneously moves 3D cursor proxy in the 3D visualization application, display, mark areas of interest with points and/or lines, which can be exported to IVT for display, step 716. Position data in airplane coordinates, images and part information can be saved with the scan data for future reference, step 718. If additional data is needed, step 720, the remote NDI expert re-orients the pan-tilt angles of the LPS unit by selecting data points in the 2D scan integration application or 3D points in the 3D visualization application, step 722. A determination is then made if additional NDI scanning is needed at a different location, step 724. When data collection is complete the on-site support person packs up the scanning equipment, with guidance from the remote NDI expert if needed.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A system for inspecting a test article comprising:
   a 3D measurement and alignment system for determining local 3D coordinates;
   a plurality of markers positioned on a test article responsive to position designation by the 3D measurement and alignment system;
   a diagnostic imaging system for a test article, said diagnostic imaging system positioned on the test article responsive to position designation by the 3D measurement and alignment system;
   a command controller connected to the 3D measurement and alignment system and receiving two dimensional (2D) images from the diagnostic imaging system, said 2D images including the markers;
   a three dimensional (3D) computer aided design (CAD) model visualization system connected to the command controller; and,
   computer software modules incorporated in the command controller for positioning of the 3D measurement and alignment system, designating the plurality of selected alignment points with said markers positioned responsive to the alignment points designated, aligning the 2D images and 3D CAD model responsive to the local 3D coordinates, and displaying the 2D images and 3D CAD model with reciprocal registration incorporating the markers, said alignment points thereby concurrently identified in the 2D images and local 3D coordinates, said software module for aligning incorporating a scan registration matrix derived from a calibration matrix for the 3D measurement and alignment system based on the selected alignment points on the test article.

2. The system for inspecting a test article of claim 1 wherein the diagnostic imaging system is a non-destructive inspection (NDI) scanner.

3. The system for inspecting a test article of claim 2 wherein the NDI scanner is an ultrasonic scanner supported on the test article for multiple axis scanning.

4. The system for inspecting a test article of claim 1 wherein the 3D measurement and alignment system comprises a local positioning system (LPS) positioned adjacent the test article having a controller and a servo controlled video and pointing system including a video camera mounted to a pan-tilt unit and incorporating a laser pointer and range meter.

5. The system for inspecting a test article of claim 4 wherein the alignment points on the test article comprise markers placed within a scan region of the diagnostic imaging system.

6. The system for inspecting a test article of claim 1 wherein the command controller is remote from the test article.

7. The system for inspecting a test article of claim 1 wherein the software module for aligning incorporates an inverse of the scan registration matrix which transforms 3D coordinates from the 3D CAD model into the coordinate system of the 2D images whereby any point selected on the 2D image is converted into the corresponding local 3D coordinates of the test article and any point selected in the 3D CAD model is converted into 2D pixel coordinates for reciprocal registration of the images.

8. A remote non-destructive inspection (NDI) system comprising:
   a local positioning system (LPS) positioned adjacent the test article;
   a NDI scanner operable on a test article at a local site, said NDI scanner positioned on the test article responsive to position designation by the LPS;
   a three dimensional (3D) computer aided design (CAD) visualization application for a CAD model of the test article;
   a remote command controller connected to the NDI scanner, the LPS and the 3D CAD visualization application, said remote command controller having software modules for receiving two dimensional (2D) scan data from the NDI scanner and creating images therefrom, receiving 3D coordinate data from the LPS for selected alignment points, aligning the images and 3D CAD model responsive to the local 3D coordinates of the selected alignment points to be concurrently identified in the 2D images and local 3D coordinates, displaying the 2D images and 3D CAD model with reciprocal registration overlaying the selected alignment points as shown in the images and model, and re-orienting the LPS.

9. The remote non-destructive inspection (NDI) system as defined in claim 8 wherein the LPS incorporates a controller connected to the remote command controller and a servo controlled video and pointing system including a video camera mounted to a pan-tilt unit and incorporating a laser pointer and range meter.

10. The remote non-destructive inspection (NDI) system as defined in claim 8 wherein the NDI scanner is an ultrasonic scanner supported on the test article for multiple axis scanning.

11. The remote non-destructive inspection (NDI) system as defined in claim 8 wherein the software modules include a Scan Integration Application (SIA) which computes a scan registration matrix from the 2D scan data and a set of 3D alignment points on the test article based on a calibration matrix for the LPS to provide a direct mapping between 2D pixel coordinates of the 2D scan data and the 3D coordinate data.

12. The remote non-destructive inspection (NDI) system as defined in claim 11 wherein the SIA further provides 3D coordinate data to the CAD visualization application to align a presented 3D view in a 3D display field perpendicular to the 2D scan data images.

13. The remote non-destructive inspection (NDI) system as defined in claim 11 wherein the SIA computes an inverse of the scan registration matrix which transforms 3D coordinates from the 3D display field onto the 2D scan image whereby any point selected on the 2D scan display is converted into the corresponding 3D coordinates of the test article and any point selected on the 3D display field is converted into 2D pixel coordinates for reciprocal registration of the images.

14. The remote non-destructive inspection (NDI) system as defined in claim 13 wherein the LPS incorporates a controller connected to the remote command controller and a servo controlled video and pointing system including a video camera mounted to a pan-tilt unit and incorporating a laser pointer and range meter and wherein the SIA further provides 3D Coordinate Data through the calibration matrix to the LPS to move the LPS pan-tilt unit to point the laser pointer at a specific 3D location selected on the 2D scan display or 3D display.

15. A method for remote non-destructive inspection (NDI) comprising:
- placing a NDI scanner mountable to a test article at a local site;
- placing a local positioning system (LPS) positioned adjacent the test article;
- connecting the NDI scanner, LPS and a three dimensional (3D) computer aided design (CAD) visualization application for a CAD model of the test article to a remote command controller;
- designating with the LPS through the command controller a plurality of alignment points on the test article and a correct position for the NDI scanner on the test article relative to the alignment points to be concurrently identified in the 2D images and local 3D coordinates;
- receiving scan data from the NDI scanner and creating 2D scan images;
- calibrating the LPS for transmission of 3D coordinates of the test article to the remote command controller;
- calculating in the remote command controller a scan registration matrix for 2D data from the NDI scanner to 3D coordinates;
- calculating in the remote command controller an inverse scan registration matrix for 3D coordinates in the CAD model to display in the 2D scan images;
- displaying the CAD model and 2D scan images with reciprocal registration overlaying the alignment points as shown in the images and model; and,
- re-directing the LPS responsive to a selected point in the 2D scan image or CAD model with a set of 3D coordinates from the command controller.

16. The method of claim 15 wherein the step of calibrating includes placing markers on three alignment points on the test article and creating a calibration matrix with the LPS using a laser pointer/range meter.

17. The method of claim 16 wherein the step of calculating the scan registration matrix employs the calibration matrix.

18. The method of claim 15 wherein the step of re-directing comprises directing the laser pointer/range meter to the set of 3D coordinates.

* * * * *